United States Patent
Esplin

[11] Patent Number: 5,916,224
[45] Date of Patent: Jun. 29, 1999

[54] TENDON REPAIR CLIP IMPLANT

[75] Inventor: Vermon S. Esplin, El Paso, Tex.

[73] Assignee: The United States of America as represented by the Secretary of the Army, Washington, D.C.

[21] Appl. No.: 08/890,682

[22] Filed: Jul. 9, 1997

[51] Int. Cl.⁶ .................................................. A61B 17/08
[52] U.S. Cl. ...................... 606/151; 606/157; 606/152
[58] Field of Search .................... 606/151, 157, 606/152, 142, 143; 227/902

[56] References Cited

U.S. PATENT DOCUMENTS

| | | | |
|---|---|---|---|
| 3,091,828 | 6/1963 | Soltis | 606/151 |
| 3,378,010 | 4/1968 | Codling et al. | 606/157 |
| 4,414,721 | 11/1983 | Hufnagel | 128/325 |
| 5,722,982 | 3/1998 | Fereira et al. | 606/151 |
| 5,766,189 | 6/1998 | Matsuno | 606/158 |

*Primary Examiner*—Michael Buiz
*Assistant Examiner*—Tina T. D. Pham
*Attorney, Agent, or Firm*—Werten F. W. Bellamy

[57] ABSTRACT

A tendon repair clip implant system for placement on the dorsal side of a lacerated or torn tendon to allow active range of motion post tendon repair, comprises: first and second clips. Each clip comprises:

(i) two serrated sections joined by integral connecting section; the serrated sections being urgeable together to provide opposing mating teeth connection by arculate bending longitudinally around an axis of the connecting section;

ii) the repair clip further comprising two relatively flat surfaces adjoining the connecting section and having openings therein through which sutures may be threaded and drawn through a lacerated tendon to assist in holding said tendon together; the openings being centered between a plurality of spikes extending from undersides of the flat surfaces to function as tendon inserts to assist in holding the lacerated tendon together.

9 Claims, 4 Drawing Sheets

TENDON REPAIR CLIP IMPLANT

CONTRACTUAL ORIGIN OF THE INVENTION

The invention described herein may be manufactured, licensed and used by or for governmental purposes without payment of any royalties to me thereon.

FIELD OF THE INVENTION

The invention relates to a tendon repair clip implant that provides sufficient grip strength to allow active ROM post tendon repair that is low profile enough to allow intrasynovial immediate active range of motion. The tendon clip implant utilizes alternating volar prong crimping to interlock various collagen bands. Multiple dorsal spikes of the tendon repair clip implant apparatus also interlock with collagen bundles and their cross links. The tendon repair clip implant apparatus effectively works as a tension sharing device. It is placed on the side of greatest tension of the tendon, which is the dorsal side to provide more resistance to gapping.

BACKGROUND OF THE INVENTION

Hand and finger lacerations have been estimated to have an annual incidence as high as 6,946,000 in the Unites States.

Tendon injuries often occur with hand lacerations. Additionally, tendon ruptures can also occur when there is no laceration. These are most commonly due to rheumatoid arthritis or post fracture attritional rupture. Inadvertent laceration during surgery can also occur. The management of these injuries continue to challenge the most experienced of surgeons, and this is particularly bothersome, as it has been shown that sutures placed in the dorsal half of tendons create a stronger repair than the traditional way that sutures are placed in the palmer side. Over the past 20 years or so, a considerable amount of research has been conducted on understanding the anatomy, healing properties, biomechanical forces, the strengths of various repairs and rehabilitation programs post repair of flexor and extensor tendon injuries.

Ochiai et al.[1] detailed the vascular anatomy of the flexor tendons and postulated the import of the vincula and dorsally located central vascular supply. Through multiple animal and invitro studies G. Lundborg[2], and R. Gelberman et al.[3] have shown that flexor tendons have an intrinsic capacity for healing that does not require a vascular supply to the tendon itself. Their studies show that most of the tendon's nutrition comes by diffusion via the synovial fluid.

[1].N. Ochiai et al.: Vascular Anatomy of Flexor Tendons JHS 4:321, 1979.
[2].G. Lundborg: Experimental intrinsic healing of flexor tendons based upon synovial fluid nutrition. JHS 3:21–31, 1978.
[3].Gelberman, R. et al.: Tendon, in Woo SLY, Buckwalter JA (eds): Injury and Repair of the Musculoskeletal Soft Tissues. Park Ridge, Ill: AAOS, 1988, pp5–40.

Gelberman et al. has also shown that the tensile strength and gliding ability of a tendon repair is enhanced with mobilization and that the more the excursion and the frequency of the motion of the tendon, the better the final outcome. This information has given rise to various passive and limited active motion rehabilitation protocols which emphasize motion of the repaired flexor tendon.

Accordingly, the current belief is that if a repair could be achieved that would allow early active flexion and extension, this would give the best functional results. Also, it is believed, that, if repair is achieved that would allow early active flexion and extension, this would further decrease the need for close occupational therapy supervision and the need for special complex and costly splints.

At the National Hand Center in Baltimore, Maryland Union Memorial Hospital, the current estimated cost of rehabilitation for a single digit flexor tendon laceration ranges between about $2,900.00 and $3,100.00 dollars per person.

U.S. Pat. No. 4,519,392 discloses hemostasing muscle clips for needleless surgery comprising two opposing toothed jaws, a hinge connecting the jaws and an open end with a locking means. A combination of two hemostasing muscle clips connected by suture material is used in strabismus surgery, thereby eliminating the need for suture and needle.

R. Savage[4] has shown that the in vitro strength of the repair is proportional to the number of sutures crossing the repair site. His complex six stranded technique was three times as strong as the two stranded technique. However, these complicated multi-strand techniques are extremely bulky, technically difficult to perform and potentially damaging to the tendon and the vascular supply of the tendon.

[4].R. Savage: In Vitro Studies of a new method of Flexor Tendon Repair. JHS (B) 1985,:10:135–141

Currently, none of the multitude of suturing techniques are sufficiently strong enough to allow for active range of motion throughout the healing process.

Therefore, there is a need extant in the art of tendon repair techniques, to provide apparatus and techniques for achieving a repair that enables early active ranges of motion of the tendons.

SUMMARY OF THE INVENTION

One object of the present invention is to provide a tendon repair clip implant apparatus that provides sufficient grip strength to allow active ROM post tendon repair that is low profile enough to allow intra-synovial immediate active range of motion.

Another object of the invention is to provide a tendon repair clip implant apparatus having alternating volar prong crimping that serves to interlock various collagen bands.

A further object of the invention is to provide a tendon repair clip implant apparatus having multiple dorsal spikes that also interlock with the collagen bundles and their cross links.

A still further object of the invention is to provide a tendon repair clip implant apparatus that functions as a tension sharing device during the repair process.

A yet further object of the invention is to provide a non-absorbable braided suture and metal clip combination of a tendon repair clip implant that is durable enough to withstand thousands of repetitious movements of the tendon over the two to four month period of time a patient needs for rehabilitation.

A further object yet still of the invention is to provide a non-absorbable braided suture clip combination of a clip-suture-clip that allows for flexibility to negotiate the twists and turns that a tendon experiences.

Other objects of the invention will become apparent upon review of the brief description of the drawings and detailed description of the preferred embodiments of the invention.

In general, the invention is accomplished by preparing a tendon repair clip implant system for placement on the dorsal side of a lacerated or torn tendon to allow active range of motion post tendon repair, comprising:

A) a first and second clip, each clip comprising:
  i) two serrated sections joined by integral connecting means; said serrated sections being urgeable together to provide opposing mating teeth connection by arculate bending longitudinally around an axis of said connecting means;

ii) said repair clip further comprising two relatively flat surfaces adjoining said connecting means and having opening means therein through which sutures may be threaded and drawn through a lacerated tendon to assist in holding said tendon together; said openings being centered between a plurality of spike means extending from undersides of said flat surfaces to function as tendon inserts to assist in holding the lacerated tendon together.

DETAILED DESCRIPTION OF THE PREFERRED EMBODIMENTS

Figure 1:
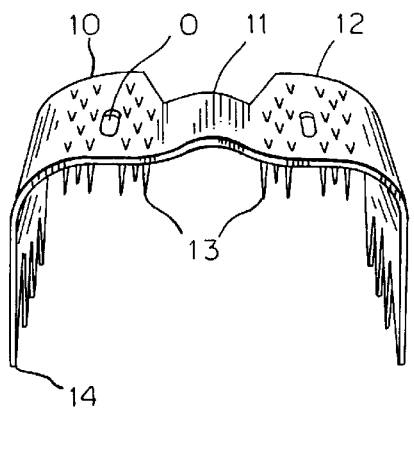
FIG. 1 shows a pre-application view in perspective of the tendon repair clip implant apparatus of the invention.

Illustrated in the drawings is an apparatus for repairing tendons that provides sufficient grip strength to allow active ROM post tendon repair that is low profile enough to allow intrasynovial immediate active ROM (Range Of Motion).

FIG. 1 shows a view in perspective of a clip 10 in its pre-application form, wherein a hinged middle section 11 connects two adjoining sections 12 containing integral spikes 13 extending therefrom, and wherein sections 12 have openings O around which base portions of spikes 13 are disposed. As can be seen from FIG. 1, the surfaces of sections 12 extend downwardly and terminate in a series of teeth or serrations 14 which serve as opposing jaws when the tendon clip is folded axially along its slightly elevated hinged section 11, as shown in the volar view of FIG. 2, wherein the teeth 14 are bent or crimped.

Figure 2:
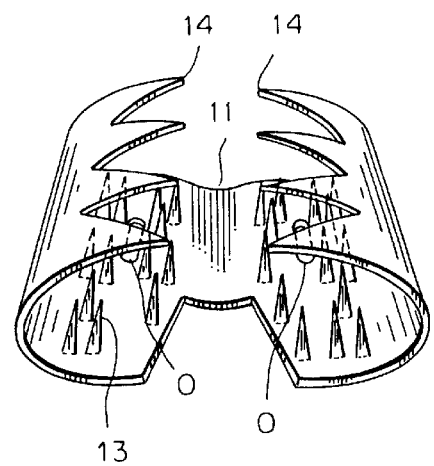
FIG. 2 shows a partially closed volar view of the tendon repair clip implant apparatus of the invention.

In FIG. 2, the opening or holes through which the sutures are placed when using the tendon repair clip implant to hold the tendon in place is now disposed at the bottom of the volar view with crimped anchors or serrations.

Figure 3:
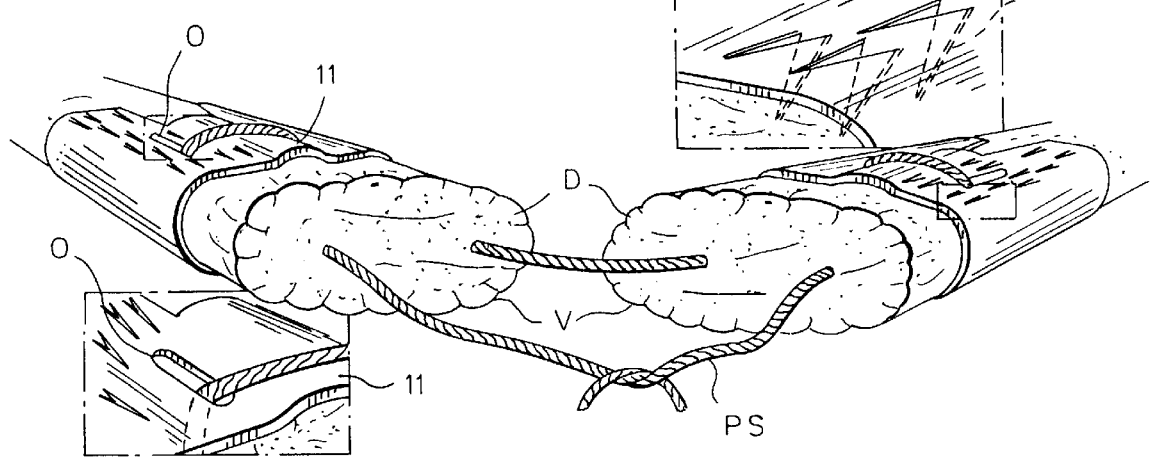
FIG. 3 is a separated view of a ruptured tendon wherein an enlarged cross section detail show a beveled edge to prevent suture rupture, and an enlarged detailed view of dorsal spikes in the tendon is shown.

FIG. 3 depicts a severed tendon sectioned to show the dorsal D and volar V regions, wherein the tendon clips of the invention have been crimped about the tendons so that the slightly elevated hinged portions of the clamp 11 are disposed on top. As can be seen in FIG. 3, a permanent suture PS has been placed through the tendons and threaded through the openings O, as can best be seen from the enlarged projected square section of the left side view of the severed tendon. The enlarged projected square section from the right side view of the severed tendon of FIG. 3 depicts a detailed view of dorsal spikes (ghosted or phantomed).

Figure 4:
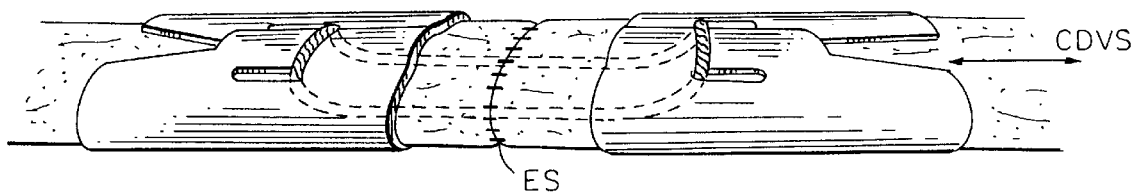
FIG. 4 shows a view of a torn tendon with the tendon repair clip implants fixed thereon, with the dorsal perforations omitted, but showing epitendinous suture.

A complete joining of the severed tendon of FIG. 3 is shown in FIG. 4, wherein a series of epitendinous sutures ES is apparent, and the central dorsal vascular supply CDVS is shown by the two arrowed line.

Figure 5:
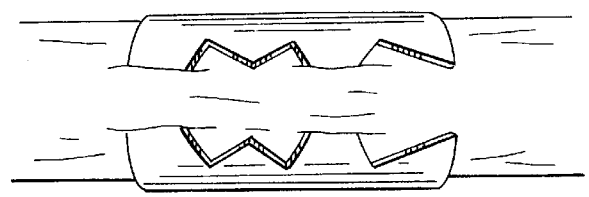
FIG. 5 is a volar view showing a crimping sequence to maximize fiber lock using the tendon repair clip implant of the invention.

FIG. 5 is a volar view showing the crimping sequence of the repair clip that is utilized to maximize fiber lock.

In practicing the invention, the design of the tendon clip implant is such as to spare or maintain the blood supply to the tendon, which already has a limited vascular supply. Tendons, although attached to muscles have a completely different structure and means of vascular supply than muscles, and this is especially the case with flexor tendons.

Finger flexor tendons must glide upwards of 6–8 centimeters within a tube or sheath, and as a consequence, their vascular supply can only enter at the ends of the tube and the sites of tendon attachments. This permits remarkable motion without being tethered by the vessels. In fact, it is the dorsal aspect of the tendon where the main blood supply travels.

Therefore, the tendon clip must not crush the tendon at one point, as this would effectively cut-off the blood supply to the rest of the tendon down stream, and would cause the rupture of a normal non-injured tendon and thereby interfere with the healing of a newly repaired tendon.

The tendon clip of the invention has a slightly elevated segment to protect the dorsal central artery and veins, and no intratendinous prongs are placed in the midline where the main vessels run.

Also, the intratendinous prongs of the tendon clip of the invention is designed to hold the configuration of the tendon so that the tendon is not crushed or strangulated of its blood supply even as it gets pulled around a pulley/bone along its course. The configuration of the design of the tendon repair clip implant of the invention allows it to be placed dorsally or volarly without disrupting the blood supply.

The design of the tendon repair clip implant of the invention is also an acknowledgment of the fact that a second way that tendons receive nutrition is by diffusion through the surrounding synovial fluid that the tendon is bathed in. This is accomplished by designing the tendon repair clip implant so that it has in it, multiple fenestrations to allow the fluid access to the tendon fiber producing cells.

Further, the tendon repair clip implant design of the invention is designed to spread out the gripping force over a larger area along the axis of the tendon, and the edges of the tendon repair clip implant are beveled so that the tendon fibers will not be cut as the tendon bends around the pulleys that guide the tendons. For example, the tendon may need to bend >90° around some pulleys.

The tendon clip is designed to be as thin and yet as strong as possible because the clip will need to withstand forces of at least ten times what the eye muscles referred to in U.S. Pat. No. 4,519,392 can generate, and yet fit within a sheath that is closely matched in contour and size with the tendon. Because of the significant amount of excursion around various pulleys and bones that a tendon must travel, the clip of the invention must also have a low profile that will not catch on any of these structures. Preferably, the clip will be made of metals (i.e. titanium and surgical steel, etc.), as these would have the strength per unit area needed to withstand the necessary forces and yet be able to be contoured close enough to the tendon to allow gliding.

In the case of implants used to surgically repair organs such as muscles or tendons, in order for the materials to be absorbed by the body there must be an inflammatory reaction to degrade the material. This creates scarring which is fine for the muscles in the eye (as is the case with U.S. Pat. No. 4,519,392) as it helps hold the cut ends of the muscle together, but excess scarring in a tendon tethers the tendon to the scar and prevents the movement/gliding of the tendon—thereby creating a stiff, useless repair.

As stated in U.S. Pat. No. 4,519,392, the muscle clip is only expected to hold the muscles ends for approximately two weeks because with the rich blood supply of the muscle that is the time it takes for the ends of the muscle to scar down.

However, tendon repairs take an average of six to eight weeks to heal and then another four to six weeks to mature because of their unique anatomy, and their limited vascular supply and the amount of force that can potentially be generated by the forearm muscles. For these reasons, a tendon clip would need to be durable enough to withstand thousands of repetitions over this two to four month period of time as the patient undergoes rehabilitation. The non-absorbable braided suture and metal clip combination of the tendon repair clip implant of the invention meets these requirements.

While there are some loose similarities between the tendon clip of the invention and the muscle clip disclosed in U.S. Pat. No. 4,519,392, under close scrutiny, it is apparent that their basic design and purpose are fundamentally different. This is because the purposes and requirements are different—for example, the muscle clip design disclosed in U.S. Pat. No. 4,519,392 is for purposes of grasping a relatively broad flat rich vascular tissue to provide hemostasis for a short period of time and resist the relatively small force of an eye muscle whereas the tendon clip of the invention is configured and designed to grasp an oval poorly vascularized tissue without injuring the vascular supply or the diffusion of nutrients to the vital cells for a prolonged period of time and still resist the significant force of the forearm muscles.

Figure 6:
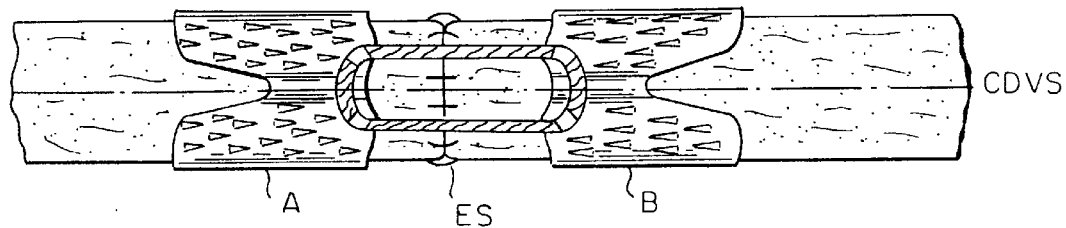
FIG. 6 shows a dorsal view of another embodiment of the invention, fixed about a torn or lacerated tendon using spikes having different angles.
Figure 7:
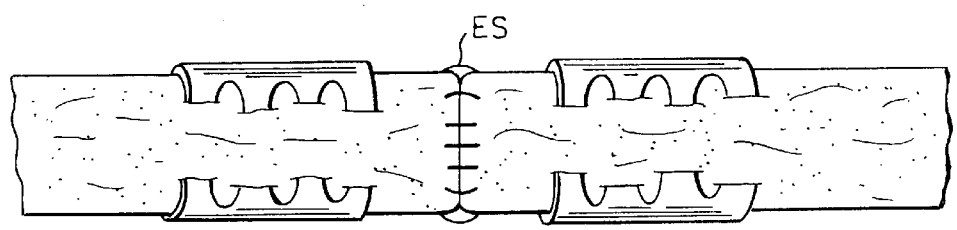
FIG. 7 shows a volar view of the tendon repair clip implant fixed about a lacerated tendon.

An alternative version of the tendon repair clip implant-combination non-absorbable braided suture is shown in FIG. 6, wherein clamps having spikes disposed at different angles are used together as option A and option B. FIG. 6 is a dorsal view of a tendon sutured in place in combination with the clip, and showing the central dorsal vascular supply CDVS for the tendon. FIG. 7 shows a volar view of FIG. 6 wherein the epitendinous suture ES common to both the dorsal and volar view is shown.

Figure 8A:
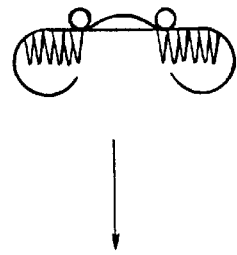
FIG. 8 shows axial views of two different embodiments of the tendon repair clip implant of the invention.
Figure 8B:
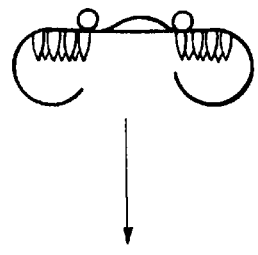

FIG. 8 shows the option A axial view and the option B axial view of the differently angled spikes from the tendon clips used together in FIGS. 6 and 7.

Figure 9A:
FIG. 9 depicts side views of the barbed sections of two different embodiments of the tendon repair clip implant of the invention, wherein the barbs are straight and curved, and wherein the arrow shows the line of tension on the tension side of the tendon or the dorsal side.
Figure 9B:
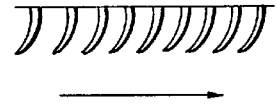

FIG. 9 depicts a side view of the barbs or spikes from the clip of option A, wherein the barbs are disposed at a 45° angle and the direction of the arrow shows the line of tension in the tendon, and a side view of the spikes of the option B tendon clip, wherein the angled spikes are curved, and the line of tension in the tendon is shown by the direction of the arrow.

In general, the sequence of application of the tendon repair clip implant of the invention, given the recent research on volar or dorsal suture placement, is applied to the dorsal aspect of the tendon for greatest benefit. However, if the anatomy or area of application makes this difficult, volar placement may be employed.

Figure 10:
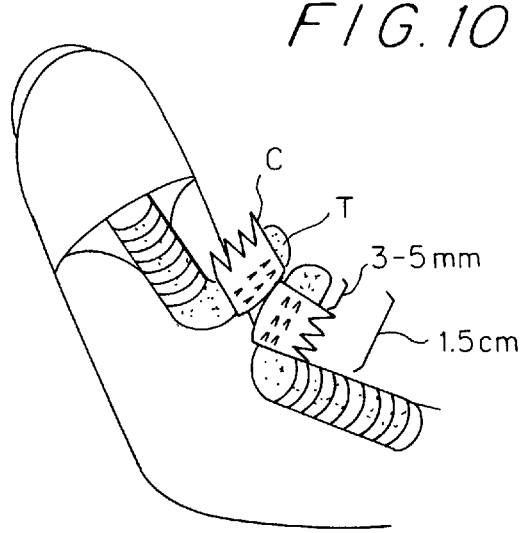
FIG. 10 depicts a finger with torn tendons with the clip of the invention positioned on the dorsal surface of each tendon.

In the application of the tendon repair clip implant, the beginning step is to expose the cut ends of the tendons T by at least 1–1.5 centimeters, whereupon the edges of the tendons are trimmed back to healthy tendons if the ends are frayed, as can be seen in FIG. 10. After preparation of the tendon ends, the tendon is sized and the appropriate sized clip C is then applied. The width of the tendon should equal the width of the clip prior to crimping, and the tendon clip is placed on the dorsal surface of each tendon end approximately 3–5 millimeters from the end of the tendon, as shown in FIG. 10.

Figure 11:
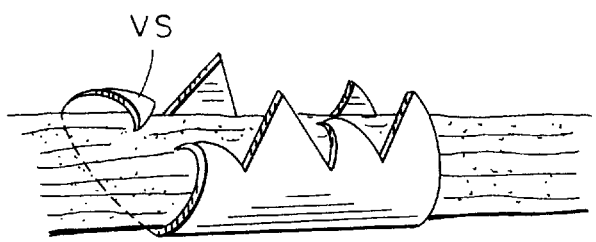
FIG. 11 shows the clip with some of its prongs crimped to engage or penetrate the volar surface of the tendon.
Figure 12:
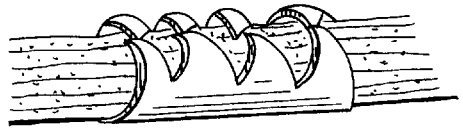
FIG. 12 depicts the clip with its remaining set of prongs crimped to grab or engage different bundles of collagen fibers.
Figure 13:
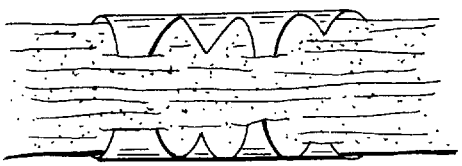
FIG. 13 is a top view of FIG. 11.
Figure 14:
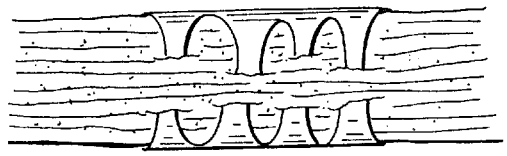
FIG. 14 is a top view of FIG. 12.

The first set of prongs or serrated sections and alternate prongs thereafter are crimped until they engage and penetrate the volar surface VS of the tendon, as shown in FIG. 11. Next, the second set of prongs or serrated sections and their alternates are crimped in like manner as the first to obtain fully crimped prongs as shown in FIG. 12. By separately crimping alternate prongs, the prongs will grab or engage different bundles of collagen fibers to provide a better grip on the tendon and pull the tendon into the multiple locking spikes on its dorsal surface.

Figure 15:
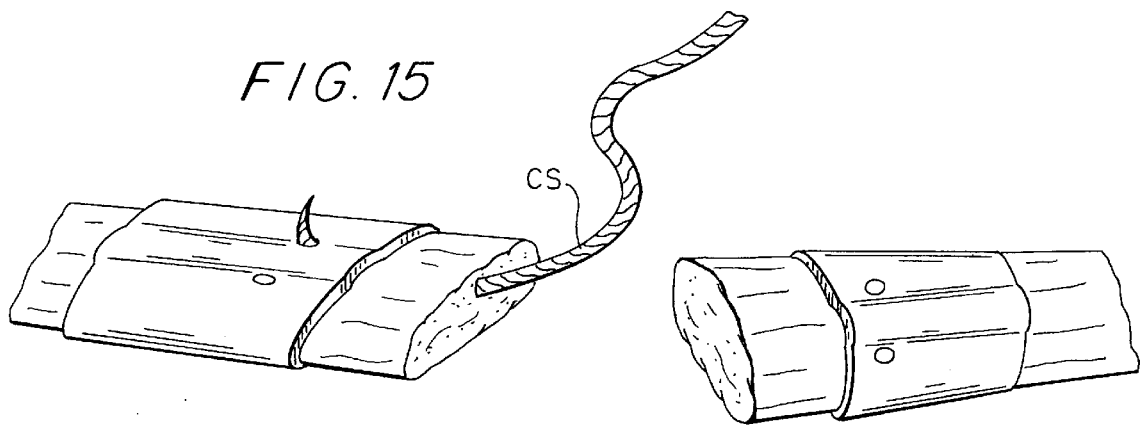
FIG. 15 depicts two cut ends of a tendon with crimped clips in place with the first throw of the core suture entering the cut surface midway between the volar and dorsal surfaces of the tendon on one side, and wherein the suture is passed up through one of the suture holes in the tendon clip on the same side.
Figure 16:
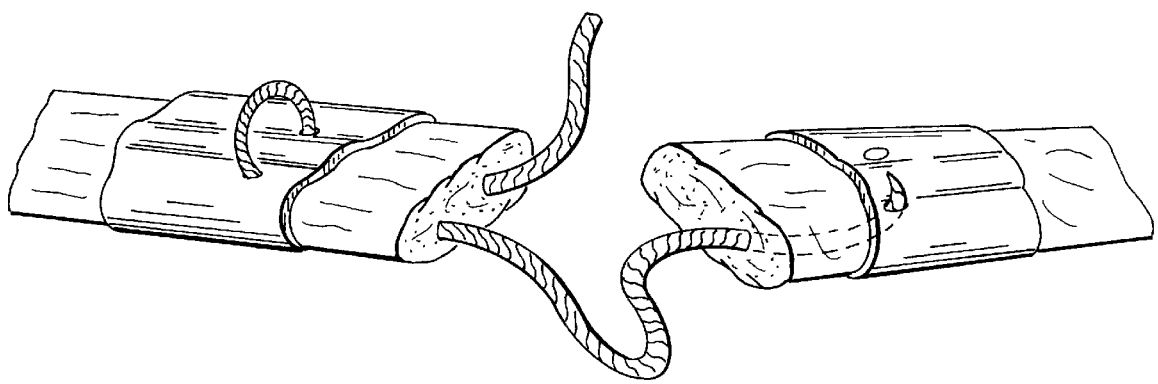
FIG. 16 shows a severed tendon wherein the course of the suture has been passed down through the adjoining suture hole shown in FIG. 15 and drawn through the cut surface near the opposite side of its starting entry, and passed through the second cut surface and up through one of the suture holes.
Figure 17:
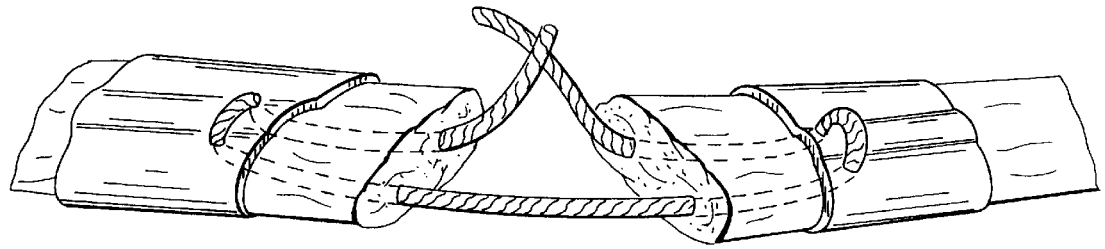
FIG. 17 depicts a severed tendon, as in FIG. 15 wherein the suture has been drawn through the adjoining suture hole on the right hand side of the tendon and further drawn so as to exit the area opposite of its entry and obtain enough loose suture between the severed tendon gap to enable tying of a knot.
Figure 18:
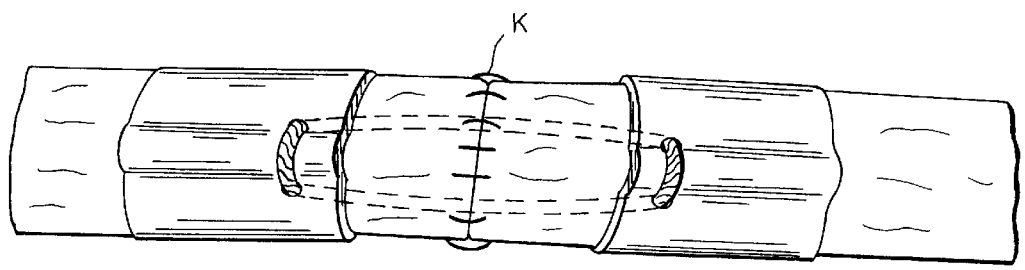
FIG. 18 shows a knot tied in the area between the severed tendon, after the tendon is drawn together by pulling on the loose ends of the suture in the gap between the severed tendon.

After crimping, the core suture CS is placed starting at the cut surface of one of the ends of the tendon as shown in FIG. 15. The first throw should enter the cut surface midway between the volar and dorsal surfaces of the tendon on one side, whereupon the suture is passed up through the suture hole in the tendon clip on the same side, as depicted in FIG. 15. Next, as can be seen in FIG. 16, the suture is passed down through the suture hole on the other side of the same clip and brought out through the cut end of the tendon again. The same procedure is followed on the other end matching the cut ends so that the suture goes straight across the opposite tendon end. The suture ends should end up on the same side of the tendon in the gap between the ends, as can best be seen in FIG. 17. The suture is then tied tight enough to bring the cut ends together with a very slight buckle of the fibers. In this connection, it should be noted that the suture must not be tied too tightly so that the ends are bunched-up, because such bunching will shorten the tendons too much. Thereafter, a secure knot K is tied in the tendon, as can be seen in FIG. 18. It should be noted that the knot will be in between the cut ends using this technique. Alternately, the suture can be placed such that the knot is tied at any place along this suture path. Also, two sutures can be used, one in each end, but this requires two knots (one on each side) which could make the repair somewhat bulky.

While any well known suture size will suffice, it is preferred that a 2-0 or 3-0 sized permanent suture is the most appropriate size to provide sufficient strength for the core suture.

While the apparatus and method of the invention have been described with reference to preferred embodiments, it will be apparent to those skilled in the art that changes and modifications may be made to the invention without departing from the spirit and scope of the invention.

I claim:

1. A tendon repair clip implant system for placement on the dorsal side of a lacerated or torn tendon to allow active range of motion post tendon repair, comprising:
    a first and second clip, each clip comprising:
        i) two serrated sections joined by integral connecting means; said serrated sections being urgeable together to provide opposing mating teeth connection by arcuate bending longitudinally around an axis of said connecting means;
        ii) said repair clip further comprising two relatively flat surfaces adjoining said connecting means and having opening means therein through which sutures may be threaded and drawn through a lacerated tendon and knotted to hold said tendon together; said openings being centered between a plurality of spike means extending from undersides of said flat surfaces to function as tendon inserts to assist in holding the lacerated tendon together; A) said connecting means being an elevated hinged section relative to said two flat surfaces; and B) said spike means on said first and said second clips extend from said undersides of said flat surfaces at different angles.

2. The tendon repair clip implant system of claim 1 wherein said spike means of said second clip is curved in relation to the spike means of said first clip.

3. The tendon repair clip implant system of claim 1 wherein said plurality of spike means extending from the undersides of said flat surfaces are intratendinous prongs configured to hold the tendon so that the tendon is not crushed or strangulated of its blood supply as the tendon is pulled around a pully/bone along its course.

4. The tendon repair clip implant system of claim 1 wherein said elevated hinged section is of sufficient height that it does not interfere with or obstruct blood flow of the central artery and veins.

5. The tendon repair clip implant system of claim 1 formed of materials selected from the group consisting of titanium and surgical steel.

6. In combination, the tendon repair clip implant system of claim 1 in place around a joined lacerated tendon.

7. A method for repairing a lacerated tendon to allow active range of motion, comprising:
    A) exposing the ends of lacerated tendons and trimming the ends of any frayed tendons back to healthy;
    B) applying an appropriate sized clip from said first and second clips of said tendon repair clip implant system of claim 1 so that the width of the tendon is equal to the width of the clip prior to crimping, by placing the clip on the dorsal surface in proximity to the end of each tendon;
    C) crimping a first set of serrated sections until they engage and penetrate the volar surface of the tendon, and crimping an alternate set of serrated sections to engage and penetrate additional volar surfaces of the tendon;
    D) placing a core suture starting at a first cut surface of one of the tendon ends so that the first throw enters said cut surface about mid-way between the volar and dorsal surfaces of the tendon on one side, passing the suture up through the suture hole in said tendon clip on the same side, passing the suture down through the suture hole on the opposite side of the same clip and bringing the suture out through the cut end of the tendon;
    E) applying the procedure in step D) to a cut surface opposite the first cut surface so that the suture ends up on the same side of the tendon in a gap between the ends; and
    F) pulling the suture tight enough to bring the cut ends together with a slight buckle of the fibers, and tying a secure knot in proximity to the juncture in the tendon.

8. The method of the claim 7, wherein a sized 2-0 to 3-0 permanent suture is used.

9. The method of claim 7, wherein in step A), the ends of the lacerated tendons are exposed for at least 1 to about 1.5 centimeters.

* * * * *